United States Patent
Wang et al.

(10) Patent No.: US 10,815,348 B2
(45) Date of Patent: Oct. 27, 2020

(54) AESCULIN STURGEON SKIN GELATIN FILM WITH ANTIOXIDANT ACTIVITY AND ENTEROCOCCUS FAECALIS DETECTION ABILITY AND A METHOD OF PREPARING THE SAME

(71) Applicants: Xuechuan Wang, Xi'an (CN); Ouyang Yue, Xi'an (CN); Xinhua Liu, Xi'an (CN); Taotao Qiang, Xi'an (CN); Longfang Ren, Xi'an (CN); Lei Tian, Xi'an (CN); Minyi Jia, Xi'an (CN); Xingke Ju, Xi'an (CN); Chengyuan Liang, Xi'an (CN)

(72) Inventors: Xuechuan Wang, Xi'an (CN); Ouyang Yue, Xi'an (CN); Xinhua Liu, Xi'an (CN); Taotao Qiang, Xi'an (CN); Longfang Ren, Xi'an (CN); Lei Tian, Xi'an (CN); Minyi Jia, Xi'an (CN); Xingke Ju, Xi'an (CN); Chengyuan Liang, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 166 days.

(21) Appl. No.: 16/027,193

(22) Filed: Jul. 3, 2018

(65) Prior Publication Data

US 2019/0031840 A1 Jan. 31, 2019

(30) Foreign Application Priority Data

Jul. 31, 2017 (CN) .......................... 2017 1 0636187

(51) Int. Cl.
*C09H 3/00* (2006.01)
*C08J 5/18* (2006.01)
*B65D 65/46* (2006.01)
*C08L 89/06* (2006.01)
*G01N 33/569* (2006.01)

(52) U.S. Cl.
CPC .............. *C08J 5/18* (2013.01); *B65D 65/466* (2013.01); *C08L 89/06* (2013.01); *C09H 3/00* (2013.01); *G01N 33/56911* (2013.01); *C08J 2389/06* (2013.01); *C08L 2201/06* (2013.01); *C08L 2201/08* (2013.01); *C08L 2201/10* (2013.01); *C08L 2201/14* (2013.01); *C08L 2203/16* (2013.01); *G01N 2333/335* (2013.01); *G01N 2333/4603* (2013.01)

(58) Field of Classification Search
None
See application file for complete search history.

(56) References Cited

U.S. PATENT DOCUMENTS

2018/0094167 A1* 4/2018 Liang ....................... B05D 1/18

OTHER PUBLICATIONS

Liang, C. et al. Edible Sturgeon Skin Gelatine Films . . . J of Functional Foods 37:219-228, Oct. 2017. (Year: 2017).*

* cited by examiner

Primary Examiner — Ralph J Gitomer

(57) ABSTRACT

A method of preparing an aesculin sturgeon skin gelatin with antioxidant activity and *Enterococcus faecalis* detection ability includes: 1) mixing a sturgeon skin gelatin and distilled water in a ratio of 1:15-1:25 (w/v) at 50-70° C. and filtering to obtain a sturgeon skin gelatin solution; 2) adding aesculin and a glycerin solution to the sturgeon skin gelatin solution, stirring the resulted sturgeon skin gelatin solution at 30-50° C. for 30 minutes, and filtering; and 3) removing air bubbles from the sturgeon skin gelatin solution of step 2) under reduced pressure, placing the sturgeon skin gelatin solution on an acrylic glass, and drying the sturgeon skin gelatin solution at in a vented oven 25° C. and 45-55% relative humidity for 24 hours to obtain the aesculin sturgeon skin gelatin film.

7 Claims, 10 Drawing Sheets

Film under natural light

Film under UV (365 nm)

Film under natural light 48 hours after *Enterococcus faecalis* infection

Film under UV (365 nm) 48 hours after *Enterococcus faecalis* infection

AESCULIN STURGEON SKIN GELATIN FILM WITH ANTIOXIDANT ACTIVITY AND ENTEROCOCCUS FAECALIS DETECTION ABILITY AND A METHOD OF PREPARING THE SAME

The present invention claims priority to Chinese Patent Application No. CN 201710636187.8, filed on Jul. 31, 2017, which is incorporated by reference for all purposes as if fully set forth herein.

FIELD OF THE INVENTION

The present invention relates to the field of food packaging, specifically, an aesculin sturgeon skin gelatin film with antioxidant activity and *Enterococcus faecalis* detection ability and a method of preparing the aesculin sturgeon skin gelatin film.

BACKGROUND OF THE INVENTION

With the continuous improvement of people's living standards, food safety and environmental protection become more and more important. The use of edible or biodegradable green packaging materials has become a hot research area in the field of food packaging. Gelatin is a collagen protein prepare by protein denaturation, and has the common properties of macromolecule proteins. At the same time, gelatin has special physicochemical properties due to its special molecular structure, for example, good film forming properties, good mechanical properties, high resistance and strength, anti-oxidation, biocompatibility and degradability. It can be used to prepare gelatin film materials. In recent years, the fish product processing industry has grown rapidly, resulting in a large amount of fish skin wastes during processing. If it cannot be fully utilized, it will not only pollute the environment but also cause waste of resources. Therefore, research and development of fish skin and fish skin gelatin products have gained much attention.

Aesculin is one of the main chemical components of Chinese traditional medicine, Qinpi (Cortex Fraxini), and has anti-inflammatory, antibacterial, diuretic and anti-tumor effects and can be used to treat eye diseases and gout and prevent cancer.

The present invention uses the less studied sturgeon skin gelatin. Aesculin is added to a sturgeon skin gelatin solution to prepare an aesculin sturgeon skin gelatin film using a film liquid plate method. Experiments show that aesculin can significantly enhance the anti-oxidation effect of gelatin film, and effectively improve the mechanical property, the water solubility and the transmittance of gelatin film.

SUMMARY OF THE INVENTION

In one embodiment, the present invention provides a method of preparing an aesculin sturgeon skin gelatin film with antioxidant activity and *Enterococcus faecalis* detection ability. The method includes the following steps: 1) mixing a sturgeon skin gelatin and distilled water in a ratio of 1:15-1:25 (w/v) at 50-70° C. and filtering to obtain a sturgeon skin gelatin solution; 2) adding aesculin and a glycerin solution to the sturgeon skin gelatin solution, a ratio of the sturgeon skin gelatin:aesculin:the glycerin solution being 1:0.3:0.2-1:0.6:0.2, stirring the resulted sturgeon skin gelatin solution at 30-50° C. for 30 minutes, and filtering, the glycerin solution containing 30% (wt) fish skin collagen; and 3) removing air bubbles from the sturgeon skin gelatin solution of step 2) under reduced pressure, placing the sturgeon skin gelatin solution on an acrylic glass, and drying the sturgeon skin gelatin solution in a vented oven at 25° C. and 45-55% relative humidity for 24 hours to obtain the aesculin sturgeon skin gelatin film.

In another one embodiment, in step 1), the ratio of the sturgeon skin gelatin and distilled water is 1:20.

In another one embodiment, in step 1), the sturgeon skin gelatin and distilled water is mixed at 60° C.

In another one embodiment, in step 2), the ratio of the sturgeon skin gelatin: aesculin:the glycerin solution is 1:0.5: 0.1.

In another one embodiment, in step 2), the sturgeon skin gelatin solution was stirred at 45° C.

In another one embodiment, in step 3), removing the air bubble is conducted by using a rotary evaporator.

In one embodiment, the present invention provides an aesculin sturgeon skin gelatin film which includes a sturgeon skin gelatin, aesculin, and a glycerin solution containing 30% (wt) fish skin collagen.

In one embodiment, the present invention provides a method of detecting *Enterococcus faecalis*. The method includes providing the aesculin sturgeon skin gelatin film of claim 7; and detecting *Enterococcus faecalis*.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
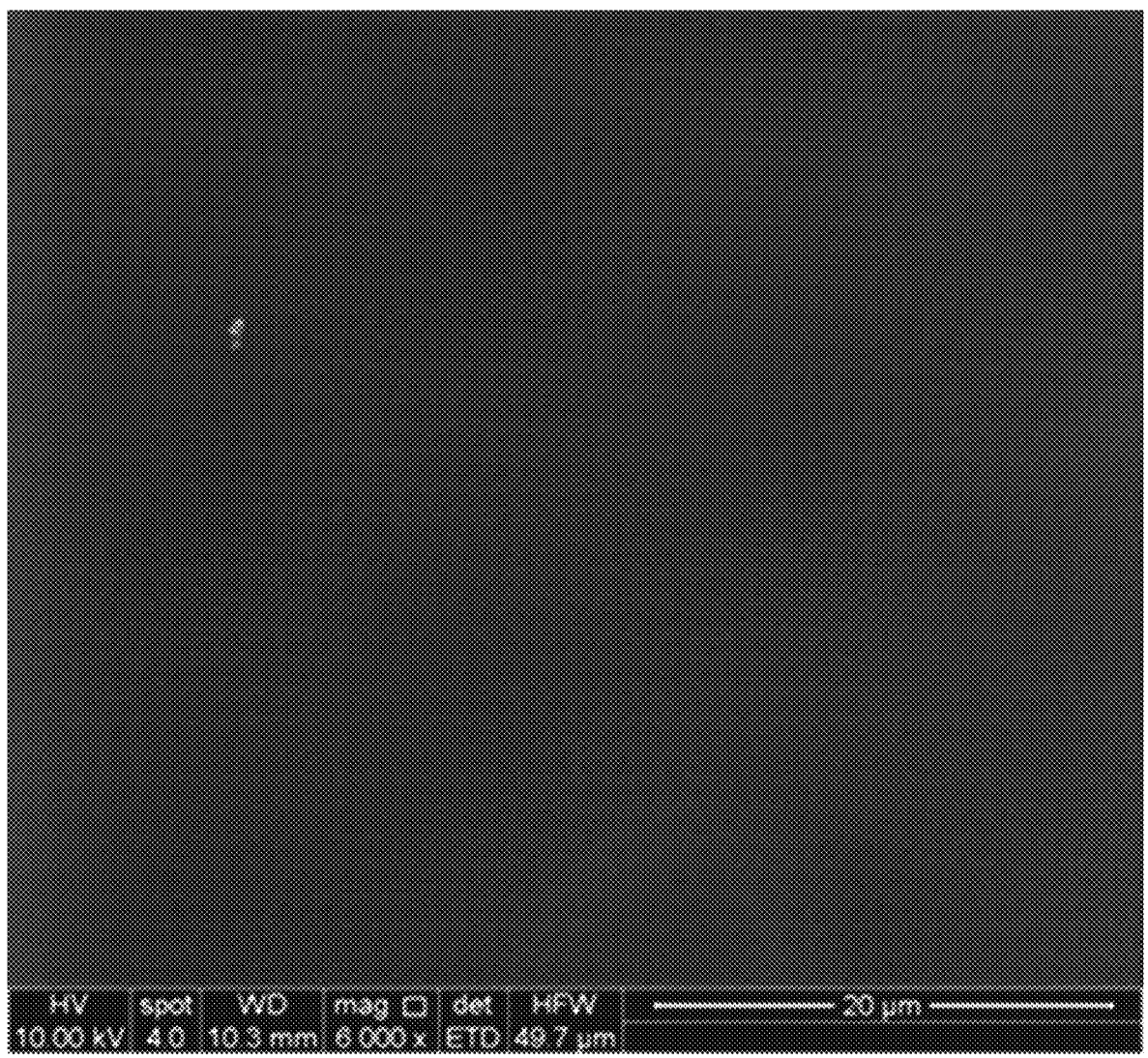
FIG. 1 shows the surface structure of sturgeon skin gelatin film.

Reference will now be made in detail to embodiments of the present invention, example of which is illustrated in the accompanying drawings. The following examples illustrate the present invention, but the present invention is not limited to the following examples.

EXAMPLE 1

This example uses 1000 grams Cortex Fraxini and 235 grams sturgeon skin as starting materials and includes the following steps.

(1) Preparation of aesculin: 1000 grams Cortex Fraxini were added to 95% ethanol in a 600 mL flask, and the mixture was heated at 70° C. water bath for 2 hours and filtered to get an ethanol extraction solution. This process was repeated 3 times, and the ethanol extraction solutions were combined and concentrated. The concentrated ethanol extraction solution was diluted with 100 mL water and then extracted with chloroform (equal volume) twice. The aqueous solution was extracted with ethyl acetate (equal volume) twice. The aqueous solution was filtered to give a yellow crystalline product, crude aesculin. The crude aesculin was purified by fresh chromatography. The eluent was methanol:dichloromethane (1:10) at a flow rate of 3 BV/h. Fractions were detected at 254 nm using an ultraviolet (UV) detector. The product was the recrystallized in method to give 25 grams aesculin as powder, a yield of 2.5%.

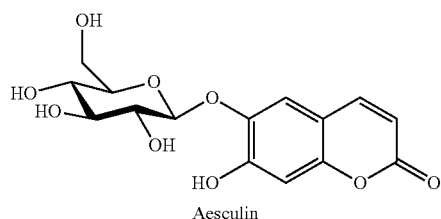

Aesculin (2) Preparation of sturgeon skin gelatin: 235 grams sturgeon skin were mixed with a 0.1 M NaOH alkali solution containing 1% $H_2O_2$ (v/v) in a sturgeon skin/alkaline solution ratio of 1/20 (w/v), and the mixture was stirred at a speed of 400 rpm for 24 hours at room temperature, and the alkali solution was replaced every 8 hours. The alkali treated sturgeon skin was then treated with 10% isopropanol (v/v) for 4 hours to remove grease and washed with ice water to neutral or slightly alkaline. After degreasing, the sturgeon skin was soaked in 0.05 M acetic acid at a ratio of 1:10 (w/v) sturgeon skin/solution at 4° C. for 4 hours, gently stirred, washed with distilled water to neutral. The sturgeon skin was then soaked in 10× distilled water (w/v), and continuously stirred until the fish skin gelatin was extracted. The gelatin solution was centrifuged at room temperature for 30 minutes, and the supernatant was concentrated, freeze-dried and stored at 4° C. The resulting gelatin is 50 grams, a yield 21.28%.

(3) Preparing of aesculin sturgeon skin gelatin film: 50 grams sturgeon skin gelatin from step (2) were added to 1000 mL distilled water, and the mixture was stirred at 60° C. to complete dissolve the sturgeon skin gelatin. The resulted sturgeon skin gelatin solution was filtered (single filter paper), and 25 grams aesculin and 5 grams glycerin solution (containing 30% (w/w) fish skin collagen) were added to the sturgeon skin gelatin solution, and the mixture was stirred at 45° C. for 30 minutes, and filtered (double filter papers). Air bubbles were removed from the sturgeon skin gelatin solution under reduced pressure using a rotary evaporator. The sturgeon skin gelatin solution was evenly placed on an acrylic glass (15×15 $cm^2$), and dried in a vented oven at 25° C. and 50±5% relative humidity for 24 hours to obtain an aesculin sturgeon skin gelatin film. The film was removed from the plate and stored in a desiccator.

EXAMPLE 2

This example uses 1000 grams Cortex Fraxini and 235 grams sturgeon skin as starting materials and includes the following steps.

(1) Preparation of aesculin: 1000 grams Cortex Fraxini were added to 95% ethanol in a 600 mL flask, and the mixture was heated at 70° C. water bath for 2 hours and filtered to get an ethanol extraction solution. This process was repeated 3 times, and the ethanol extraction solutions were combined and concentrated. The concentrated ethanol extraction solution was diluted with 100 mL water and then extracted with chloroform (equal volume) twice. The aqueous solution was extracted with ethyl acetate (equal volume) twice. The aqueous solution was filtered to give a yellow crystalline product, crude aesculin. The crude aesculin was purified by fresh chromatography. The eluent was methanol:dichloromethane (1:10) at a flow rate of 3 BV/h. Fractions were detected at 254 nm using an ultraviolet (UV) detector. The product was the recrystallized in method to give 25 grams aesculin as powder, a yield of 2.5%.

(2) Preparation of sturgeon skin gelatin: 235 grams sturgeon skin were mixed with a 0.1 M NaOH alkali solution containing 1% $H_2O_2$ (v/v) in a sturgeon skin/alkaline solution ratio of 1/20 (w/v), and the mixture was stirred at a speed of 400 rpm for 24 hours at room temperature, and the alkali solution was replaced every 8 hours. The alkali treated sturgeon skin was then treated with 10% isopropanol (v/v) for 4 hours to remove grease and washed with ice water to neutral or slightly alkaline. After degreasing, the sturgeon skin was soaked in 0.05 M acetic acid at a ratio of 1:10 (w/v) sturgeon skin/solution at 4° C. for 4 hours, gently stirred, washed with distilled water to neutral. The sturgeon skin was then soaked in 10× distilled water (w/v), and continuously stirred until the fish skin gelatin was extracted. The gelatin solution was centrifuged at room temperature for 30 minutes, and the supernatant was concentrated, freeze-dried and stored at 4° C. The resulting gelatin is 50 grams, a yield 21.28%.

(3) Preparing of aesculin sturgeon skin gelatin film: 50 grams sturgeon skin gelatin from step (2) were added to 750 mL distilled water, and the mixture was stirred at 50° C. to complete dissolve the sturgeon skin gelatin. The resulted sturgeon skin gelatin solution was filtered (single filter paper), and 25 grams aesculin and 5 grams glycerin solution (containing 30% (w/w) fish skin collagen) were added to the sturgeon skin gelatin solution, and the mixture was stirred at 50° C. for 30 minutes, and filtered (double filter papers). Air bubbles were removed from the sturgeon skin gelatin solution under reduced pressure using a rotary evaporator. The sturgeon skin gelatin solution was evenly placed on an acrylic glass (15×15 $cm^2$), and dried in a vented oven at 25° C. and 50±5% relative humidity for 24 hours to obtain an aesculin sturgeon skin gelatin film. Comparing with the film of Example 1, the film of Example 2 was difficult to remove from the plate and has poor transmittance.

EXAMPLE 3

This example uses 1000 grams Cortex Fraxini and 235 grams sturgeon skin as starting materials and includes the following steps.

(1) Preparation of aesculin: 1000 grams Cortex Fraxini were added to 95% ethanol in a 600 mL flask, and the mixture was heated at 70° C. water bath for 2 hours and filtered to get an ethanol extraction solution. This process was repeated 3 times, and the ethanol extraction solutions were combined and concentrated. The concentrated ethanol extraction solution was diluted with 100 mL water and then extracted with chloroform (equal volume) twice. The aqueous solution was extracted with ethyl acetate (equal volume) twice. The aqueous solution was filtered to give a yellow crystalline product, crude aesculin. The crude aesculin was purified by fresh chromatography. The eluent was methanol:dichloromethane (1:10) at a flow rate of 3 BV/h. Fractions were detected at 254 nm using an ultraviolet (UV) detector. The product was the recrystallized in method to give 25 grams aesculin as powder, a yield of 2.5%.

(2) Preparation of sturgeon skin gelatin: 235 grams sturgeon skin were mixed with a 0.1 M NaOH alkali solution containing 1% $H_2O_2$ (v/v) in a sturgeon skin/alkaline solution ratio of 1/20 (w/v), and the mixture was stirred at a speed of 400 rpm for 24 hours at room temperature, and the alkali solution was replaced every 8 hours. The alkali treated sturgeon skin was then treated with 10% isopropanol (v/v) for 4 hours to remove grease and washed with ice water to neutral or slightly alkaline. After degreasing, the sturgeon skin was soaked in 0.05 M acetic acid at a ratio of 1:10 (w/v) sturgeon skin/solution at 4° C. for 4 hours, gently stirred, washed with distilled water to neutral. The sturgeon skin was then soaked in 10× distilled water (w/v), and continuously stirred until the fish skin gelatin was extracted. The gelatin solution was centrifuged at room temperature for 30 minutes, and the supernatant was concentrated, freeze-dried and stored at 4° C. The resulting gelatin is 50 grams, a yield 21.28%.

(3) Preparing of aesculin sturgeon skin gelatin film: 50 grams sturgeon skin gelatin from step (2) were added to 1000 mL distilled water, and the mixture was stirred at 60° C. to complete dissolve the sturgeon skin gelatin. The resulted sturgeon skin gelatin solution was filtered (single filter paper), and 15 grams aesculin and 10 grams glycerin solution (containing 30% (w/w) fish skin collagen) were added to the sturgeon skin gelatin solution, and the mixture was stirred at 30° C. for 30 minutes, and filtered (double filter papers). The glycerin solution was used as a plasticizing agent. Air bubbles were removed from the sturgeon skin gelatin solution under reduced pressure using a rotary evaporator. The sturgeon skin gelatin solution was evenly placed on an acrylic glass (15×15 cm²), and dried in a vented oven at 25° C. and 50±5% relative humidity for 24 hours to obtain an aesculin sturgeon skin gelatin film. Comparing with the film of Example 1, the film of Example 3 has poor antioxidant activity.

By comparing the quality of the gelatin films of Examples 1-3, the condition of Example 1 is preferred.

EXAMPLE 4

Aesculin Sturgeon Skin Gelatin Film Antioxidant Activity Measurement—DPPH Method The aesculin sturgeon skin gelatin film from Example 1 was solved in 5% SDS (sodium dodecyl sulfate), and heated with a water bath at 85° C. for 1 hour. The solution was centrifuged at room temperature. 2 mL of the supernatant from the centrifuge was added to 2 mL of 0.15 mM 2,2-diphenyl-1-picryl hydrazyl (DPPH). The mixture was mixed and incubated in the dark at room temperature for 20 minutes. Then, the mixture was centrifuged at 4000 r/min for 10 minutes. The absorbance was read at 517 nm using a spectrophotometer. The assay was conducted in triplicate. The DPPH radical scavenging activity was calculated as follows:

Scavenging activity (%)=100×[1−($A_i$−$A_j$)/$A_0$]

$A_i$, $A_j$, and $A_0$ are the absorbances of film after treatment with DPPH, film without treatment with DPPH, and control (DPPH solution), respectively.

DPPH test results are shown in Table 1.

TABLE 1

| | Scavenging Activity | | | |
|---|---|---|---|---|
| Sample | $A_0$ | $A_i$ | $A_j$ | Scavenging Activity |
| Aesculin sturgeon skin gelatin film | 0.486 | 0.421 | 0.089 | 31.7% |
| Cowhide gelatin film | 0.486 | 0.465 | 0.078 | 20.4% |

As shown in Table 1, the scavenging activity of aesculin sturgeon skin gelatin film is 31.7%, and that of cowhide gelatin film is 20.4%. The aesculin sturgeon skin gelatin film has better scavenging activity than the cowhide gelatin film.

EXAMPLE 5

Aesculin Sturgeon Skin Gelatin Film Antioxidant Activity Measurement—Reduction Method In an acidic solution, a reducing substance reacts with potassium ferricyanide to produce potassium ferrocyanide. $Fe^{2+}$ then may react with potassium ferricyanide (high concentration) to produce soluble Prussian blue. Prussian blue can be measured by the absorbance at 700 mm. Higher absorbance at 700 mm indicates greater reduction ability of the sub stance.

2 mL aesculin sturgeon skin gelatin film solution was added 2.5 mL 0.2 M phosphate buffer (pH 6.6) and 2.5 mL 1% potassium ferricyanide. The mixture was reacted at 50° C. for 20 minutes. 2.5 mL of trichloroacetic acid was added to the mixture, and the mixture was reacted at 50° C. for 20 minutes. The mixture was then centrifuged at 2000×g, 22° C., for 10 minutes. The absorbance of the resulting solution was measured at 700 nm. Using a film solution containing 1.0 mg/mL Vitamin C was used as a positive control. The results are shown in Table 2.

TABLE 2

| | Absorbance at 700 mm | | | |
|---|---|---|---|---|
| Sample | A1 | A2 | A3 | A (average) |
| Aesculin sturgeon skin gelatin film solution | 0.139 | 0.138 | 0.140 | 0.139 |
| Film solution containing vitamin C | 0.177 | 0.176 | 0.178 | 0.177 |

The reduction ability of the aesculin sturgeon skin gelatin film is similar to that of Vitamin C. The sturgeon skin gelatin film has good antioxidant activity.

EXAMPLE 6

Aesculin Sturgeon Skin Gelatin Film Thickness Measurement

The film thickness was measured using a handheld micrometer (543-690, Mitutoyo Corp., Kawasaki-shi, Japan). Five locations (4 corners and one center) on each film sample were used for determining thickness. The thickness measurement is shown in Table 3.

TABLE 3

Film Thickness

| Thickness | Measurement ($10^{-2}$ mm) | | | | | Average ($10^{-2}$ mm) |
|---|---|---|---|---|---|---|
| d1 | 5.0 | 5.3 | 5.4 | 5.1 | 4.7 | 510 |
| d2 | 4.8 | 4.9 | 5.3 | 5.6 | 4.9 | 5.10 |
| d3 | 4.9 | 5.7 | 5.6 | 4.9 | 4.7 | 5.16 |

Overall: d = (d1 + d2 + d3)/3 = 5.12 ($10^{-2}$ mm)

The aesculin sturgeon skin gelatin was evenly spread on a flat plate, so the sturgeon skin gelatin film has uniform thickness. The thicknesses of the five random positions differs by about 0.008 mm, and it can be seen that the film thickness is relatively uniform.

EXAMPLE 7

Aesculin Sturgeon Skin Gelatin Film Mechanical Properties Measurement

Tensile strength (TS) and elongation at break (E%) of films were determined by using a universal material testing machine (Lloyd Instruments plc, Fareham, Hampshire, UK). Films were conditioned at room temperature and 50±5% RH for 72 hours before the test. Eight film samples (2×5 cm$^2$) with an initial grip length of 3 cm were prepared from each film to test their mechanical properties. The average thickness of each film sample was used to estimate the cross-sectional area. The initial grip separation and mechanical crosshead speed of films was set at 30 mm/min. The maximum load and the final extension at break were used for calculating TS and EAB.

The calculation formulae are as follows:

$$TS = Fm/(d \times W)$$

In the formula: TS: tensile strength (MPa); Fm: the maximum tension (N) the specimen is subjected to when it breaks; d: thickness of the film (mm); W: the width of the film (mm).

$$EAB = (\Delta L/L_0) \times 100\% = [(L_1 - L_0)/L_0] 100\%$$

In the formula, $L_0$ is the original length of the membrane (mm); $\Delta L$ is length of the film stretched when it breaks (mm); $L_1$ is The maximum length (mm) reached when the membrane breaks.

The TS and EAB of aesculin sturgeon skin gelatin film of Example 1 and sturgeon skin gelatin film are shown in Table 4.

As shown in Table 4, after adding aesculin, the film maintains good mechanical properties.

EXAMPLE 8

Aesculin Sturgeon Skin Gelatin Film Solubility Measurement

The water solubility of the sturgeon skin gelatin film was determined. 0.250 gram of the sturgeon skin gelatin film was first dried at 105° C. in an oven to a constant weight, and then weighed ($W_0$). The film was immersed into 550 mL of distilled water for 24 hours. The mixture was centrifuged at 9000 r/min for 10 minutes. The supernatant was discarded, and the remaining gelation film at 105° C. in an oven to a constant weight, and weighted (W). The water solubility can be calculated as follows:

$$WS\ (\%) = [(W_0 - W)/W] \times 100\%$$

The water solubility of the aesculin sturgeon skin gelatin film of Example 1 is 77.81±0.02%, and that of sturgeon skin gelatin film (control) is 90.24±0.02%. The water solubility of the aesculin sturgeon skin gelatin film is average, and it is suitable for low water content food packaging. The sturgeon skin gelatin film (control) was prepared accordance with the procedure described in step (3) of Example 1 except that aesculin was not added to the sturgeon skin gelatin solution.

EXAMPLE 9

Aesculin Sturgeon Skin Gelatin Film Water Vapor Permeability Measurement

Water vapor permeability measures the amount of the water vapor passing through a unit of film with a unit of thickness, under a unit of pressure, in a unit of time. The higher water vapor permeability, the less amount of water vapor passing through the film.

Water vapor permeability (WVP) was measured. The sturgeon skin gelatin film was dried in a desiccator for 2 hours. The dried sturgeon skin gelatin film was cut into circular shape, and placed in a water vapor permeability instrument for measurement.

The WVP of the aesculin sturgeon skin gelatin film of Example 1 is 1.42±1.02×10$^{-10}$ g m$^{-1}$ pa$^{-1}$ s$^{-1}$ and that of sturgeon skin gelatin film (control) is 2.71±0.65×10$^{-10}$ g m$^{-1}$ Pa$^{-1}$ s$^{-1}$. The water vapor permeability of aesculin sturgeon skin gelatin film is low, and has good water prevention property.

EXAMPLE 10

Aesculin Sturgeon Skin Gelatin Film Light Transmittance Measurement

The sturgeon skin gelatin film was cut into 4 cm×1 cm pieces, and placed in a UV spectrophotometer for measurement at 600 nm. A high transmittance value represents the

TABLE 4

Film mechanical properties measurement

| Sample | | Measurement | | | | | | | | Average |
|---|---|---|---|---|---|---|---|---|---|---|
| Aesculin sturgeon skin gelatin film | TS (MPa) | 35.29 | 35.30 | 35.25 | 35.27 | 35.30 | 35.31 | 35.26 | 35.24 | 35.278 |
| | EAB (%) | 49.178 | 49.223 | 49.217 | 49.201 | 49.220 | 49.200 | 49.216 | 49.225 | 49.210 |
| Sturgeon skin gelatin film | TS (MPa) | 26.20 | 26.15 | 26.31 | 26.26 | 26.35 | 26.10 | 26.23 | 26.28 | 26.235 |
| | EAB (%) | 53.79 | 53.82 | 53.80 | 53.76 | 53.78 | 53.81 | 53.83 | 53.90 | 53.811 | lower transparency of film. The transmittance affects the quality of the gelatin films. Gelatin films with high transmittance are desirable and suitable for food packaging.

The transmittance of the aesculin sturgeon skin gelatin film of Example 1 is 80.04%, and that of sturgeon skin gelatin film (control) is 89.88%. The aesculin sturgeon skin gelatin film is transparent, and has good light transmission property.

EXAMPLE 11

Figure 2:
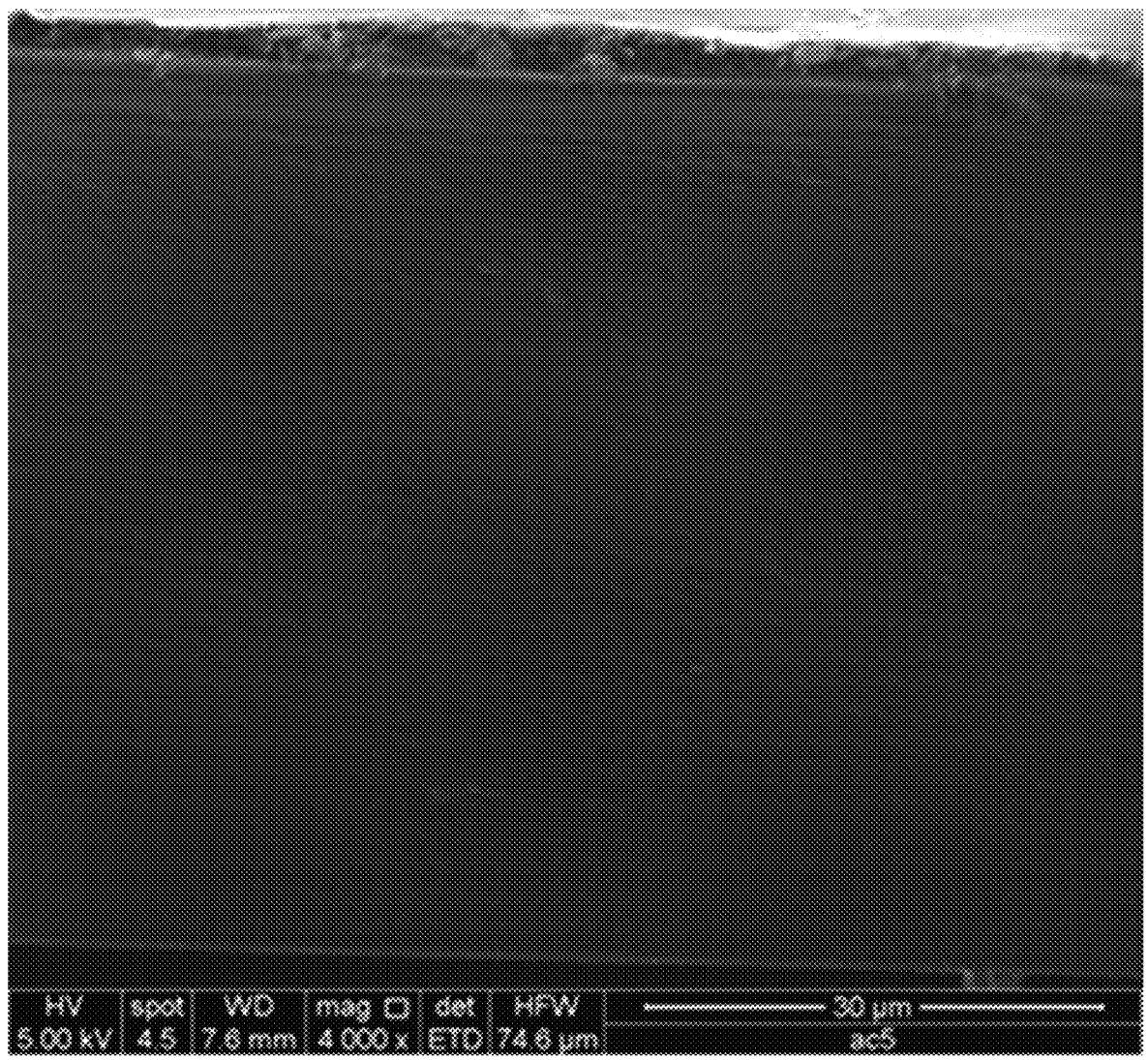
FIG. 2 shows the cross-sectional structure of sturgeon skin gelatin film.
Figure 3:
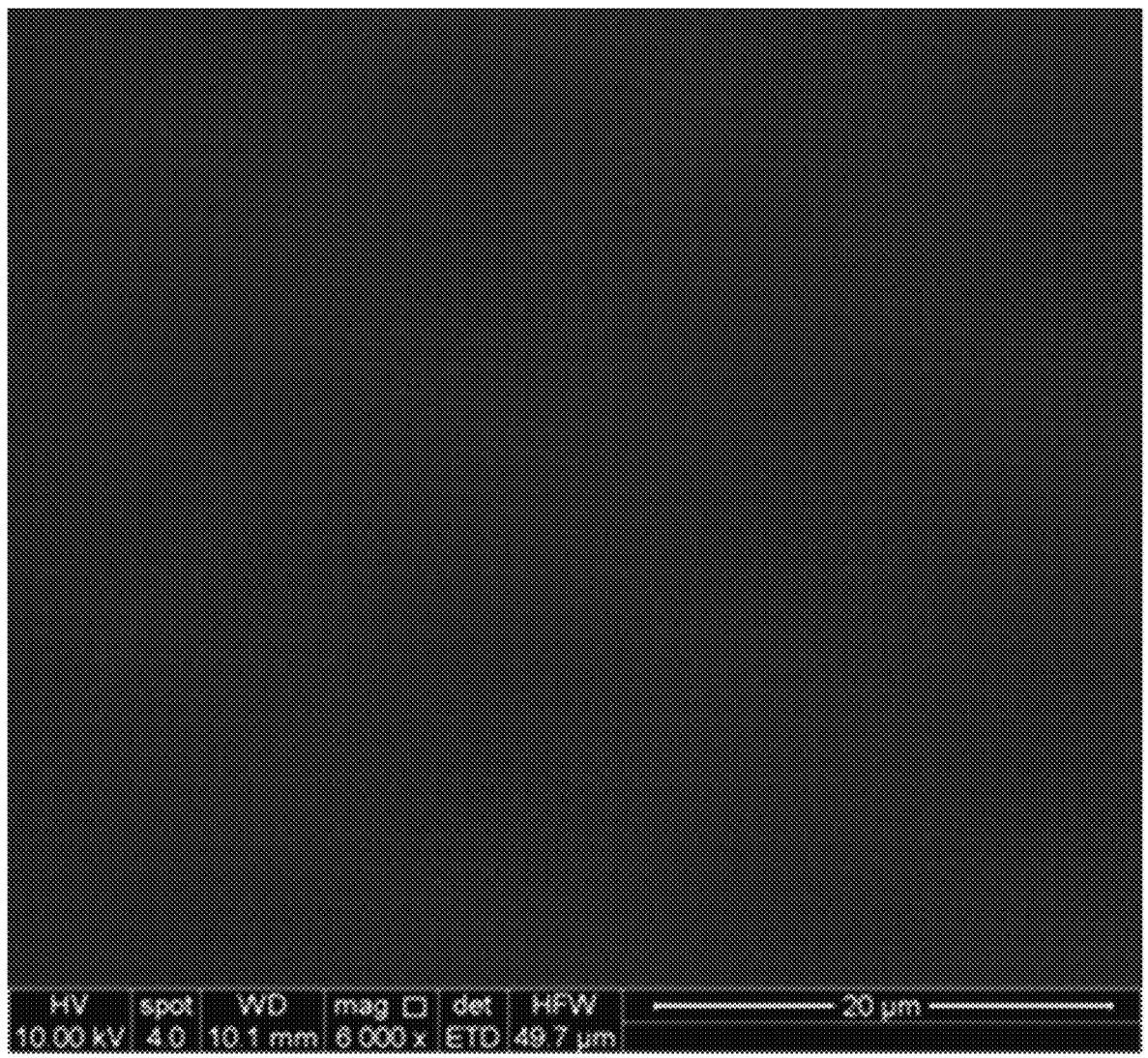
FIG. 3 shows the surface structure of aesculin sturgeon skin gelatin film.
Figure 4:
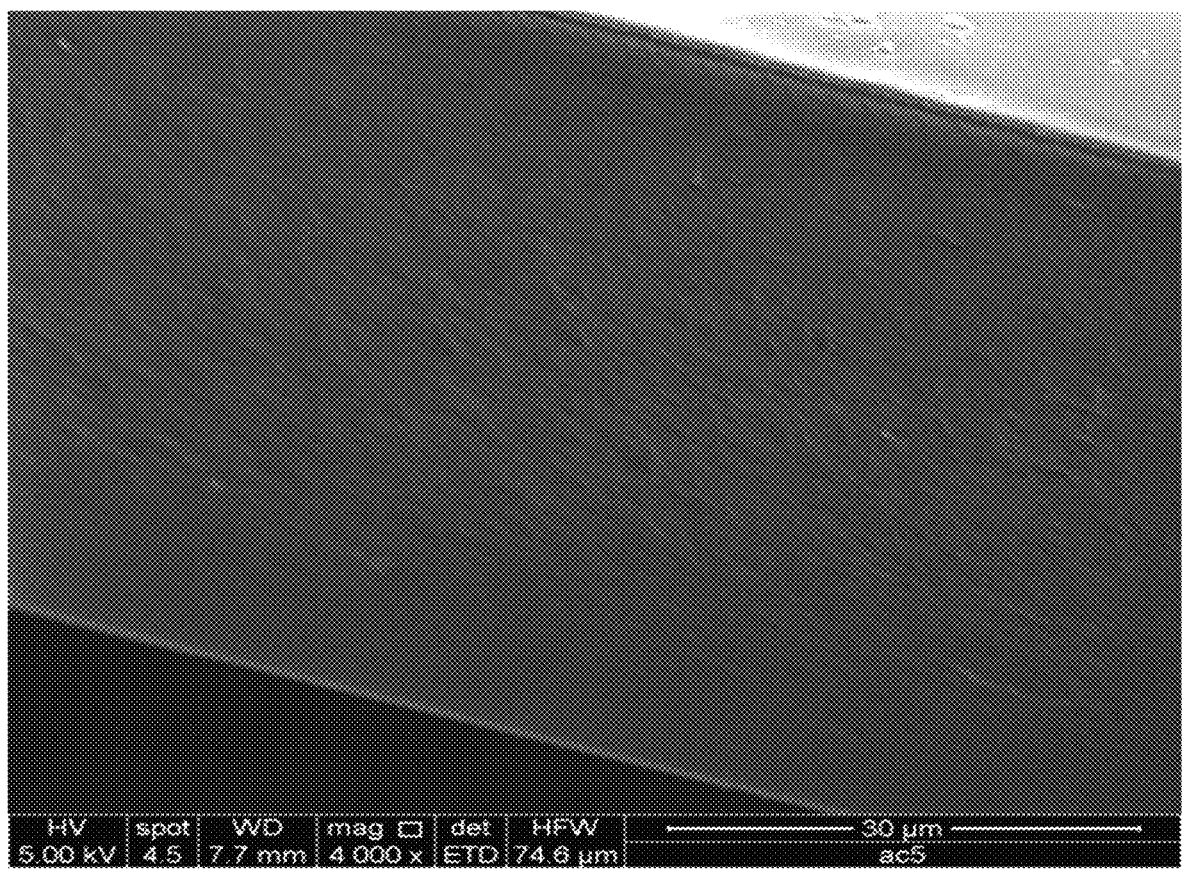
FIG. 4 shows the cross-sectional structure of aesculin sturgeon skin gelatin film.

Aesculin Sturgeon Skin Gelatin Film Characterization (1) Film Microstructure Measurement Scanning electron microscopy (SEM) analysis: The morphology of the surface and cross-section of the film samples were visualized using a scanning electron microscopy (Q45 FEI, Eindhoven, the Netherlands). Film specimens were fractured in liquid nitrogen and mounted on copper stubs perpendicularly to their surface. All samples were examined at an accelerating voltage of 10 kV. FIG. 1 shows the surface structure of sturgeon skin gelatin film; FIG. 2 shows the cross-sectional structure of sturgeon skin gelatin film; FIG. 3 shows the surface structure of aesculin sturgeon skin gelatin film; and FIG. 4 shows the cross-sectional structure of aesculin sturgeon skin gelatin film.

As shown in FIG. 1, the surface of sturgeon skin gelatin film was smooth and uniform with no brittle areas, porous structures or bubbles, and the molecules were arranged in an orderly manner. As shown in FIG. 3, the surface of aesculin sturgeon skin gelatin film was smoother than that of the sturgeon skin gelatin film. Similarly, as shown in FIGS. 2 and 4, the cross-section of aesculin sturgeon skin gelatin film has more compact structure than that of sturgeon skin gelatin film, with no granules or significant delamination. These indicate that aesculin sturgeon skin gelatin film is a homogeneous dispersion system and suitable for food packaging and preservation.

(2) Fourier-Transform Infrared (FTIR) Spectroscopy

The aesculin sturgeon skin gelatin film was placed in a desiccate containing $P_2O_5$ for 10 days to remove water content, and was then placed in the sample chamber for measurement. The resolution is set at 4 $cm^{-1}$. Fourier transform infrared spectroscopy at a full band (500-4000 $cm^{-1}$) scans to analyze the infrared spectrum of the film.

Figure 5:
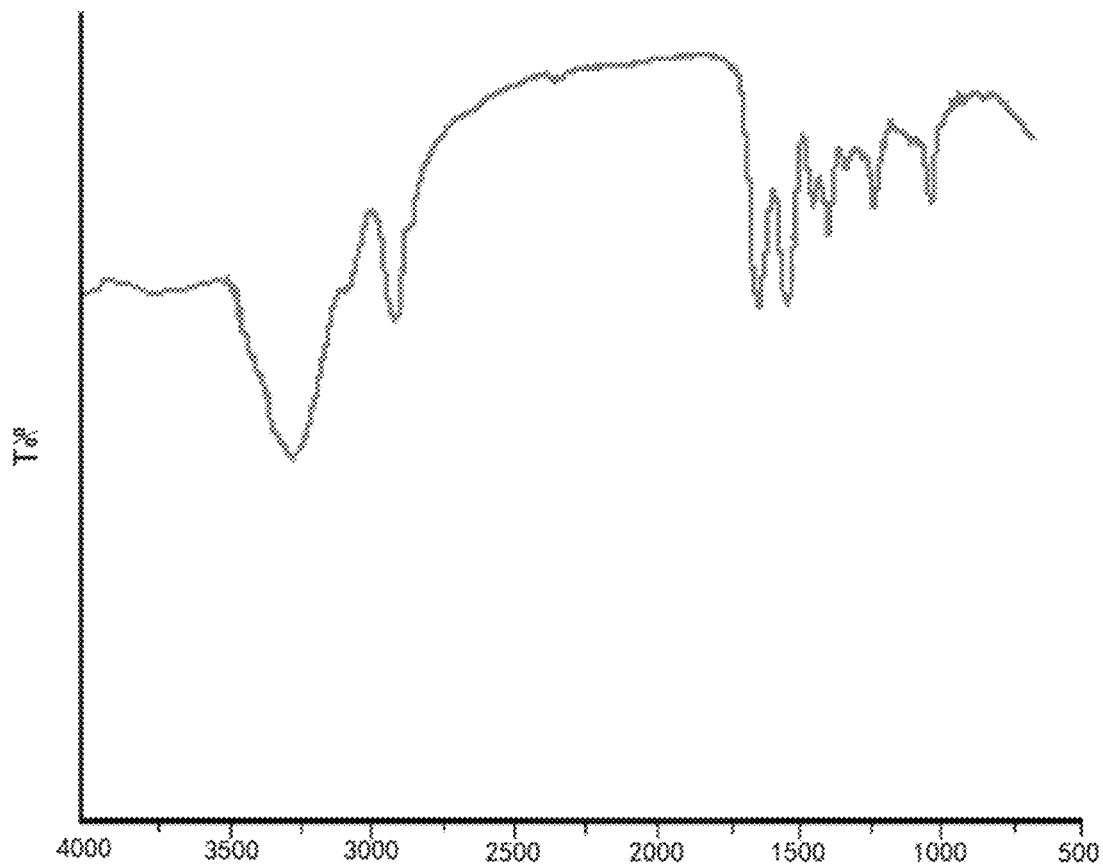
FIG. 5 is the Fourier-transform infrared (FTIR) spectroscopy of aesculin sturgeon skin gelatin film.

FIG. 5 shows that the sturgeon skin gelatin film has the following characteristic peaks:

1644.30 $cm^{-1}$:amide band I (C=O, imine C=H stretching vibration);

1543.64 $cm^{-1}$:amide band II (NH bending vibration peak);

1237.27 $cm^{-1}$:amide band III (NH deformation peak);

1398.30 $cm^{-1}$:amide band IV ($CH_2$ of proline side chains);

3266.15 $cm^{-1}$:amide band A (NH stretching vibration);

2920.15 $cm^{-1}$:amide band B (=CH and $-NH_2$ asymmetric stretching vibration peak).

FTIR results show that the incorporation of aesculin changed the molecular strucure and intermolecular interaction of the film. The interaction between gelatin and aesculin establishes forms a cross-linking and compact membrane network.

(3) Thermal Gravimetric Analysis (TGA)

Before analysis, the aesculin sturgeon skin gelatin film was conditioned in a desiccator containing $P_2O_5$ for 7 days at room temperature. Dehydrated films were scanned using a thermo-gravimetric analyzer (Q500, TA, New Castle, USA) from 20 to 600° C. at a rate of 10° C./min. Nitrogen was used as the purge gas at a flow rate of 20 ml/min. Table 5 shows Aesculin sturgeon skin gelatin film thermal degradation temperature (Td, ° C.) and weight loss (Δw, %).

TABLE 5

Film thermal degradation temperature (Td, ° C.) and weight loss (Δw, %).

| | $\Delta_1$ | | $\Delta_2$ | | $\Delta_3$ | | Residual |
|---|---|---|---|---|---|---|---|
| | $Td_1$ | $\Delta w_1$ | $Td_2$ | $\Delta w_2$ | $Td_3$ | $\Delta w_3$ | rate (%) |
| Film | 81.2 | 8.05 | 213.5 | 17.47 | 326.9 | 38.79 | 27.29 |

Note:
$\Delta_1$, $\Delta_2$, and $\Delta_3$ represent the weight loss of the film at the first, second and third stage, respectively.

Figure 6:
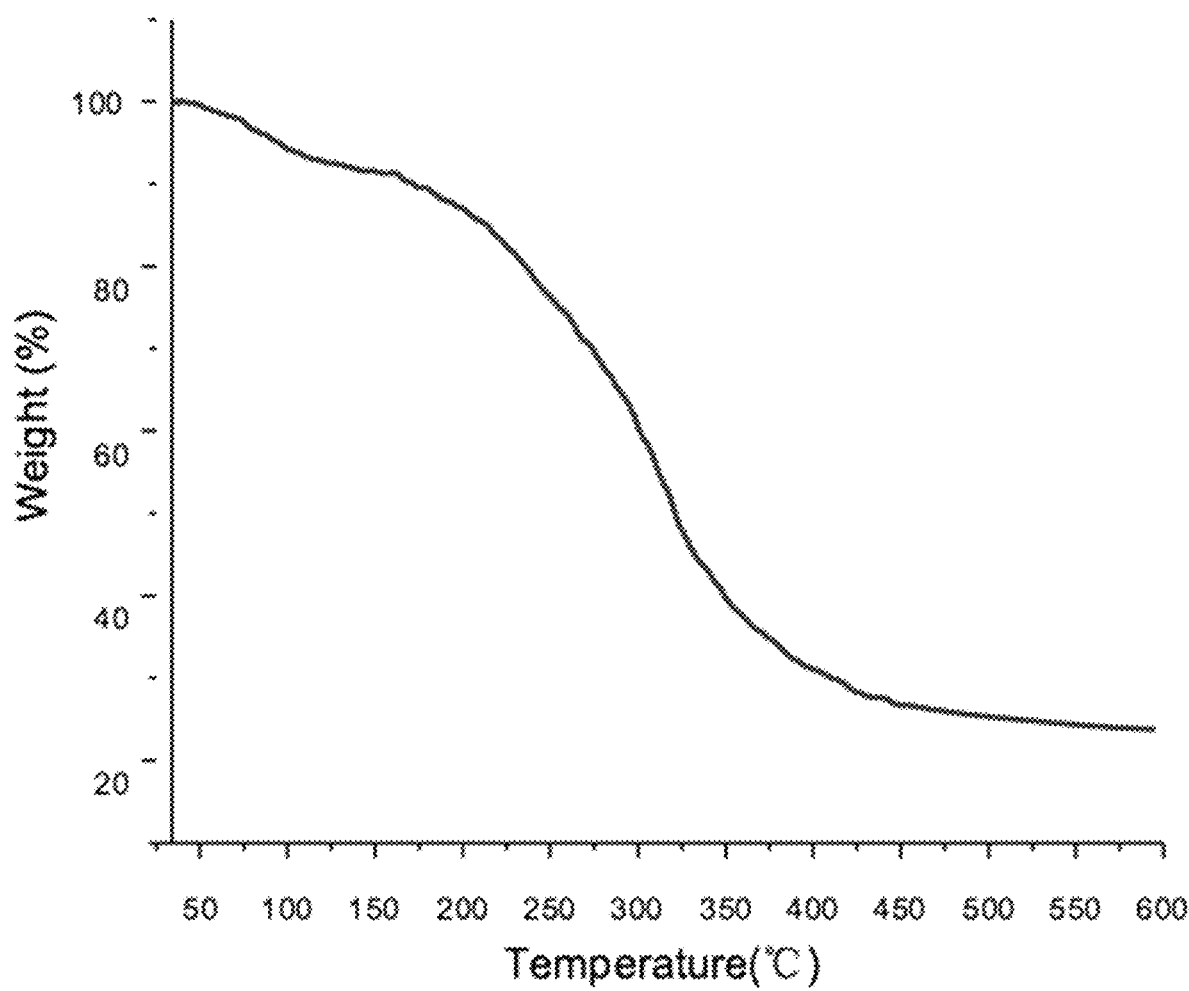
FIG. 6 shows the Thermal Gravimetric Analysis (TGA) results of aesculin sturgeon skin gelatin film.

The TGA results are shown in FIG. 6. The film shows three major weight loss stages. The first stage is 54.3-81.2° C. The film has a slow weight loss and weight loss ($\Delta_{w1}$=8.05-12.06%), which is mainly related to the loss of moisture in the film. The second stage is 156.2-213.5° C. with weight loss ($\Delta_{w2}$=17.47-19.02%). This stage may be due to the loss of low molecular weight peptides and bound water. The weight loss of the third stage was observed at 312.5-326.9° C. ($\Delta_{w3}$=38.79-51.84%). This result is mainly related to the degradation of macromolecular proteins and gelatin chains. The TGA study indicates that the incorporation of aesculin increases the thermal stability of the film. This improvement in thermal stability is important for the development of food packaging films.

(4) Differential Scanning Calorimetry (DSC)

Prior to DSC analysis, the aesculin sturgeon skin gelatin film was conditioned in a desiccator containing $P_2O_5$ for 7 days at room temperature. The analysis uses a differential scanning calorimeter, scanning from 20° C. to 200° C. at a rate of 3° C./min. Nitrogen was used as a purge gas at a flow rate of 20 mL/min.

Figure 7:
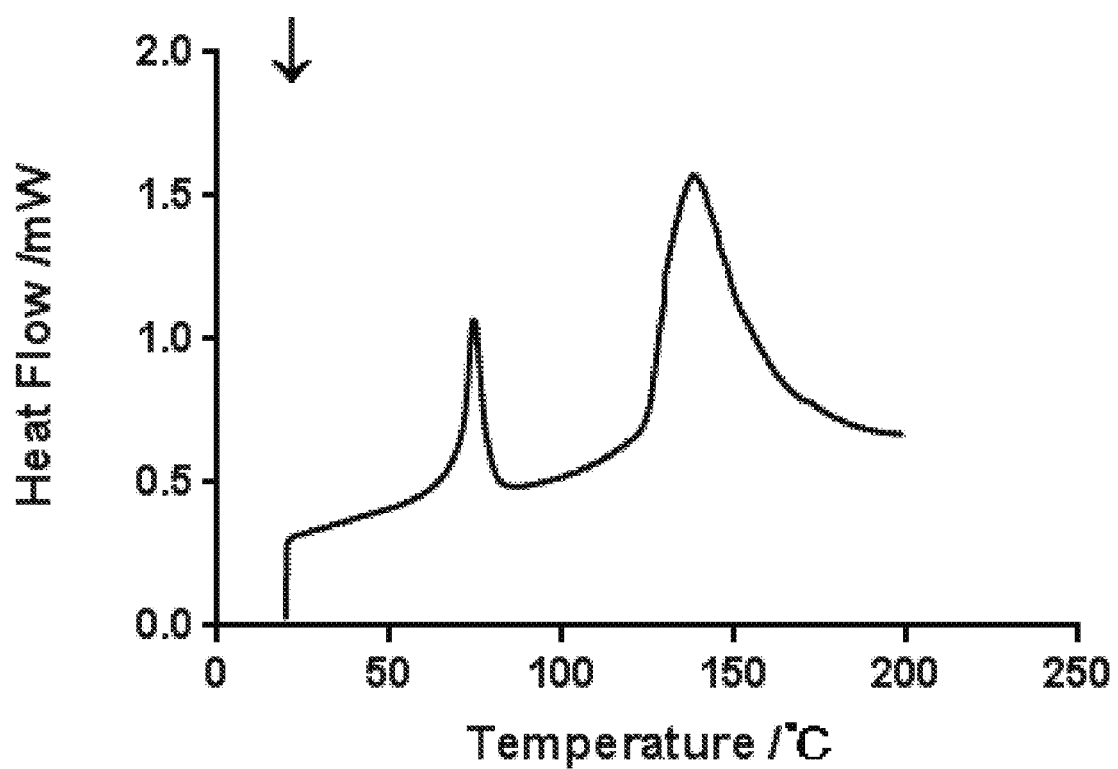
FIG. 7 shows the Differential Scanning calorimetry (DSC) of aesculin sturgeon skin gelatin film.

The DSC results are shown in FIG. 7. In the natural state, gelatin is a rod-shaped molecule that has a relatively rigid structure and contains three peptide chains. Degradation of gelatin can result in three peptide chains in a random coil state. Therefore, the thermal denaturation of gelatin is an unfolding process of three peptide chains at a relatively narrow temperature interval. The hydrogen bond breaks due to heating, causing the gelatin molecules to unfold and the molecular structure to break from an ordered and folded state to a disordered and random coil state. As shown in FIG. 7, when the temperature rises from 20° C. to 200° C., a distinct endothermic peak appears at 73.5° C. on the DSC curve, indicating that the moisture in the film is volatilized at this temperature. The endothermic peak at 136.35° C. is also evident, indicating that the film is denatured at this temperature. The degeneration temperature of the film is higher, so the aesculin sturgeon skin gelatin film has good thermal stability.

According, the aesculin sturgeon skin gelatin film has good anti-oxidation activity, thermal and mechanical stabilities, and transparency, and can be used in the research and development of food packaging films.

EXAMPLE 12

Aesculin Sturgeon Skin Gelatin Film Hydrophobicity Determination

Figure 8:
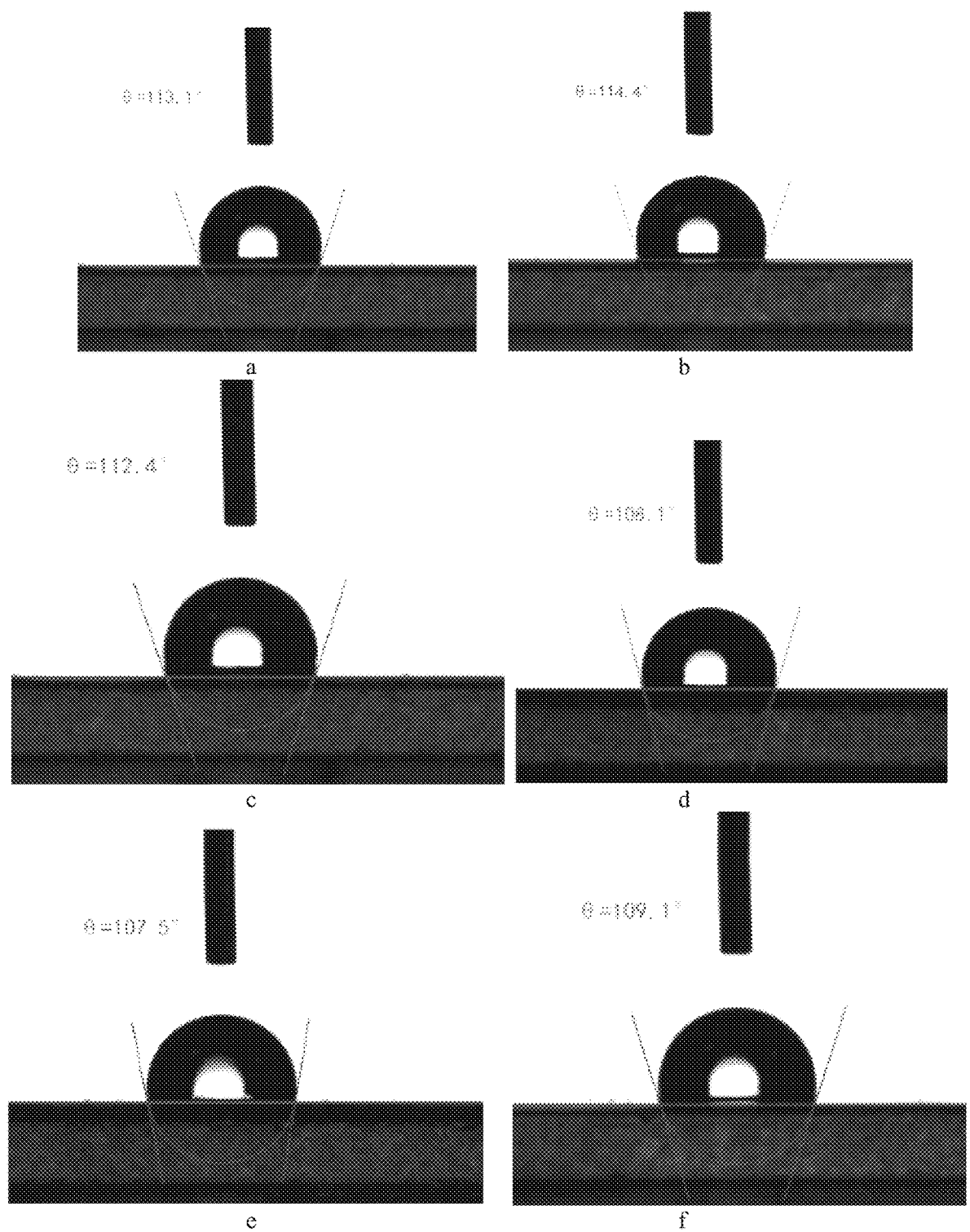
FIG. 8 shows the contact angles between the water droplets and the aesculin sturgeon skin gelatin film.

The film was cut into rectangular samples of size 0.5 cm×5 cm, and placed on a flat clean glass plate. The contact angle between the water droplets and the film was measured using a video optical contact angle tester to determine the hydrophobicity of the film. The water drop capacity was set to 5 μl. Randomly select three drops of water on the film sample, record the contact angle, and calculate the average value. The results are shown in FIG. 8 and Table 6.

TABLE 6

Aesculin sturgeon skin gelatin film contact angles

| Samples | Contact Angles | | | Average |
|---|---|---|---|---|
| Sturgeon skin gelatin film | 113.1 (a) | 114.4 (b) | 112.4 (c) | 113.3 |
| Aesculin sturgeon skin gelatin film | 108.1 (d) | 107.5 (e) | 109.1 (f) | 108.2 |

As shown in Table 6 and FIG. 8, the contact angles of the sturgeon skin gelatin film is greater than 90° and is hydrophobic; after adding the aesculin, the contact angle of the aesculin sturgeon skin gelatin film is still more than 90° and is hydrophobic. Thus, the aesculin sturgeon skin gelatin film can be used for food packaging containing a small amount of water.

EXAMPLE 13

Aesculin Sturgeon Skin Gelatin Film Relative Molecular Weight Distribution Measurement Polyacrylamide gel electrophoresis: 25 μL of the film sample (2 mg/mL) and protein molecular weight marker were mixed with loading buffer in a 1:4 ratio. The sample was placed in 100° C. water bath for 5 minutes. The sample was centrifuged at 6000 r·min$^{-1}$ for 3 min, and 10 μL supernatant was taken. After the electrophoresis was completed, the gel was shaken in a fixative solution for 1 h (70 r·min$^{-1}$), and stained with Coomassie Brilliant Blue R-250 for 30 minutes. The resulting gel electrophoresis gel was decolored by a decolorization solution. The relative molecular mass distribution of the aesculin sturgeon skin gelatin film was shown in the gel sheet (FIG. 9).

The standard protein has a molecular weight range of 53k Da-212k Da. In FIG. 9, M is the standard protein electrophoresis pattern, and A and B are the gel electrophoretograms of the aesculin sturgeon skin gelatin film.

Figure 9:
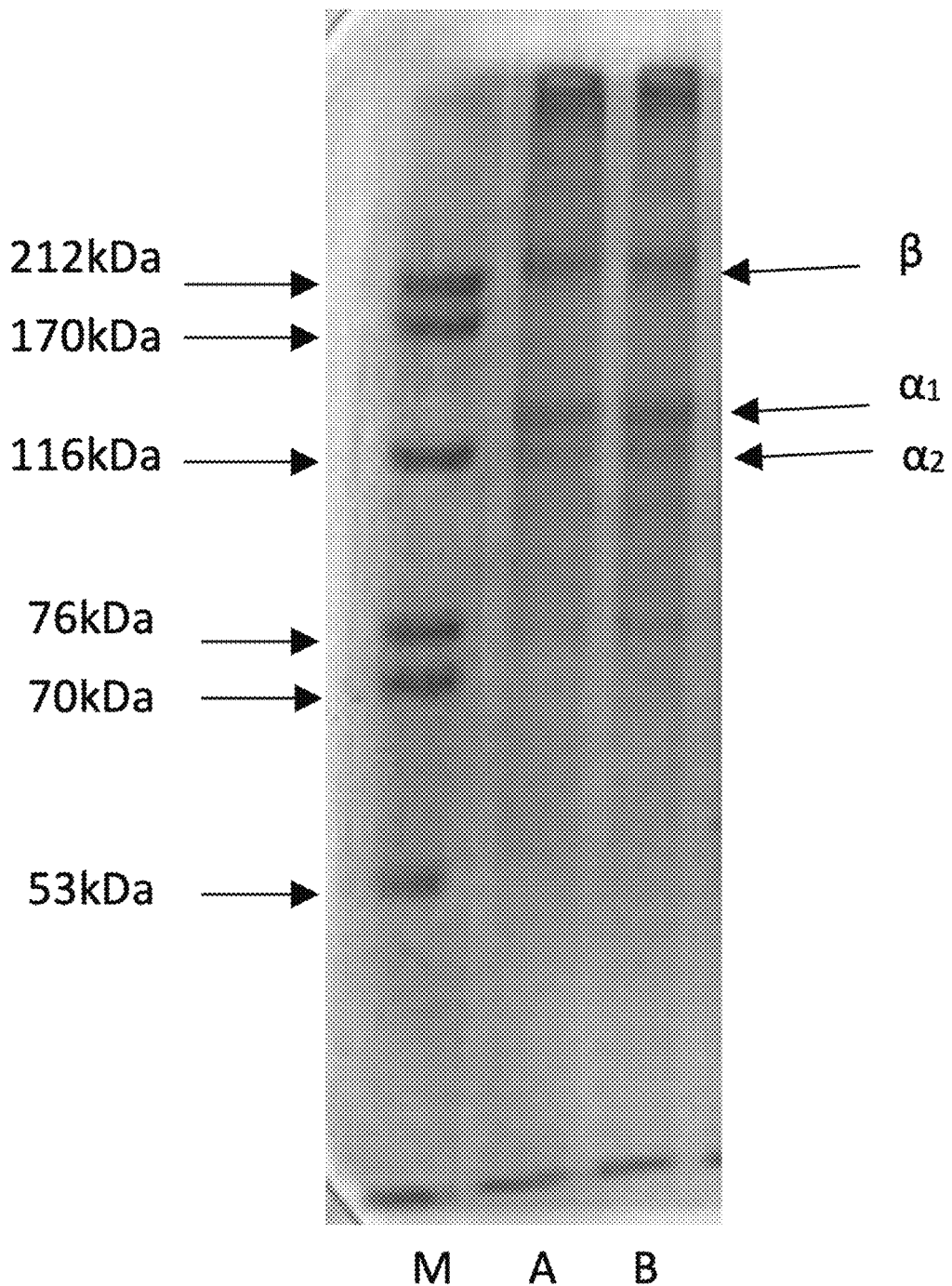
FIG. 9 shows the gel electrophoresis results of aesculin sturgeon skin gelatin film.

FIG. 9 shows that in the aesculin sturgeon skin gelatin film, the peptide chain breaks mainly to α1 and α2 components, and the α1 chain has a higher density than α2 chain. There is also a high molecular weight β chain. The relative molecular weight of the aesculin sturgeon skin gelatin film is about 126 kDa.

EXAMPLE 14

Aesculin Sturgeon Skin Gelatin Film's *Enterococcus faecalis* Detection Ability (1) Using an aesculin sturgeon skin gelatin and ferric citrate solution to draw a mouse pattern on a sturgeon skin gelatin film, and drying to obtain a self-contrast sturgeon skin gelatin film.

(2) Adding *Enterococcus faecalis* to a tube having the same diameter as a turbidimeter tube, and adding sterile distilled water to set the concentration of the bacteria to be same as same as the third tube of the McFarland standard tube.

(3) Spraying the prepared bacterial suspension from step (2) on the self-contrast sturgeon skin gelatin film prepared in step (1), and observing the color change of the film under natural light and fluorescence. The results are shown in FIG. 10.

Figure 10:
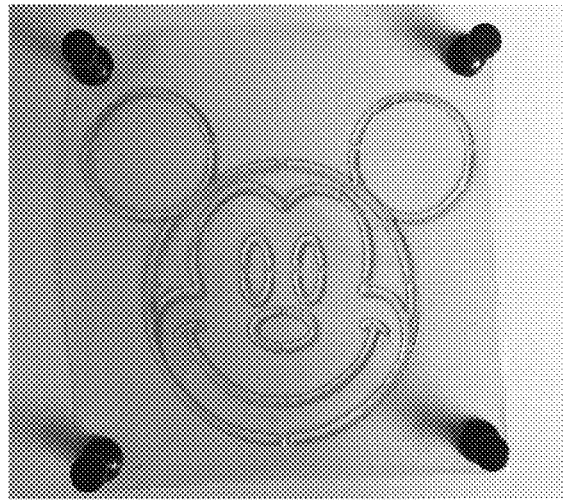
FIG. 10 shows aesculin sturgeon skin gelatin film's *Enterococcus faecalis detection ability*.
Figure 10:
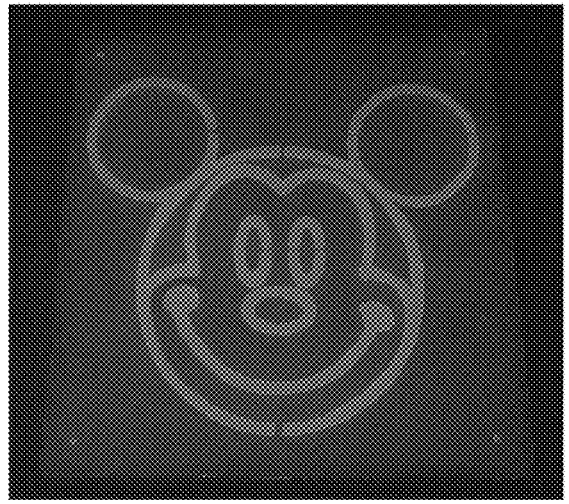
Figure 10:
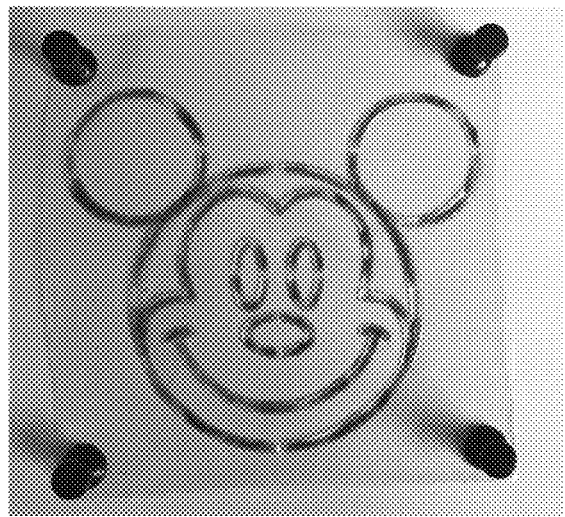
Figure 10:
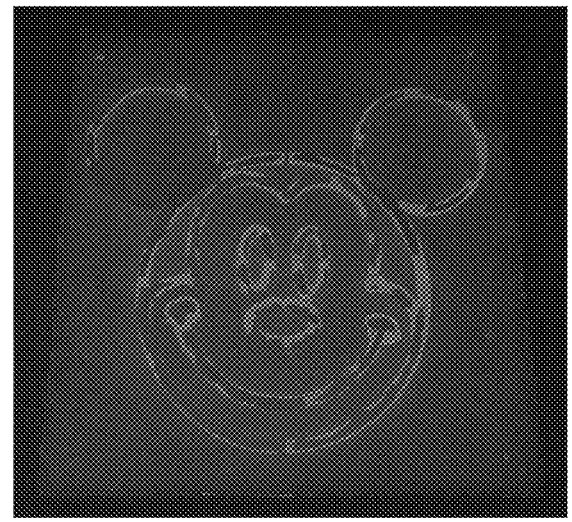

As shown in FIG. 10, aesculin has a strong fluorescence at 365 nm, and the fluorescence effect can be used to determine whether the film is contaminated. After the bacterial suspension was sprayed on the film, the change of the film was observed under natural light and ultraviolet light, respectively. When the bacterial suspension was sprayed on the film, *Enterococcus faecalis* decomposed (hydrolyzed) aesculin on the film. The resulted products were glucose and aesculetin. Aesculetin reacted with color indicator ferric citrate to form a black substance. The black substance darkened the mouse pattern on the film, which is observable under natural light. Further, the decomposition of aesculin leads to loss of fluorescence. The darkening effect and the loss of fluorescence can be used to detect *Enterococcus faecalis* infection. This detection method is fast and convenient and has high sensitivity. Thus, the aesculin sturgeon skin gelatin film is suitable for rapid detection of *Enterococcus faecalis*.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A method of preparing an aesculin sturgeon skin gelatin film with antioxidant activity and *Enterococcus faecalis* detection ability comprising the following steps:
    1) mixing a sturgeon skin gelatin and distilled water in a ratio of 1:15-1:25 (w/v) at 50-70° C. and filtering to obtain a sturgeon skin gelatin solution;
    2) adding aesculin and a glycerin solution to the sturgeon skin gelatin solution, a ratio of the sturgeon skin gelatin:aesculin:the glycerin solution being 1:0.3:0.2 to 1:0.6:0.2, stirring the resulted sturgeon skin gelatin solution at 30-50° C. for 30 minutes, and filtering, the glycerin solution containing 30% (wt) fish skin collagen; and
    3) removing air bubbles from the sturgeon skin gelatin solution of step 2) under reduced pressure, placing the sturgeon skin gelatin solution on an acrylic glass, and drying the sturgeon skin gelatin solution in a vented oven at 25° C. and 45-55% relative humidity for 24 hours to obtain the aesculin sturgeon skin gelatin film.

2. The method of claim 1, wherein in step 1), the ratio of the sturgeon skin gelatin and distilled water is 1:20.

3. The method of claim 1, wherein in step 1), the sturgeon skin gelatin and distilled water is mixed at 60° C.

4. The method of claim 1, wherein in step 2), the ratio of the sturgeon skin gelatin : aesculin:the glycerin solution is 1:0.5:0.1.

5. The method of claim 1, wherein in step 2), the sturgeon skin gelatin solution was stirred at 45° C.

6. The method of claim 1, wherein in step 3), removing the air bubbles is conducted by using a rotary evaporator.

7. An aesculin sturgeon skin gelatin film comprising:
    a sturgeon skin gelatin,
    aesculin, and
    a glycerin solution containing 30% (wt) fish skin collagen.

* * * * *